United States Patent [19]

Manoliu et al.

[11] 4,018,082
[45] Apr. 19, 1977

[54] DEVICE FOR NONDESTRUCTIVE ULTRASONIC TESTING OF CYLINDRICAL PARTS

[75] Inventors: Victor Manoliu; Andrei Lutescu; Gheorghe Ionescu; Silviu Heretoiu; Victor Frangopol; Lucuta Petru, all of Bucharest, Romania

[73] Assignee: Institutul Pentru Creatie Stintifica si Tehnica-Increst, Bucharest, Romania

[22] Filed: Sept. 30, 1975

[21] Appl. No.: 618,205

[30] Foreign Application Priority Data

Dec. 30, 1974 Romania .............................. 80986

[52] U.S. Cl. ........................... 73/67.5 R; 73/67.8 S
[51] Int. Cl.[2] ....................................... G01N 29/04
[58] Field of Search .............. 73/67.5 R, 67.6, 67.7, 73/67.8 R, 67.8 S, 67.9

[56] References Cited

UNITED STATES PATENTS

| | | | |
|---|---|---|---|
| 2,921,126 | 1/1960 | Street et al. ..................... | 73/67.6 X |
| 3,225,136 | 12/1965 | Furon ....................... | 73/67.8 S UX |
| 3,780,570 | 12/1973 | Collins ........................... | 73/67.5 R |

OTHER PUBLICATIONS

A. P. Rogel et al., A New Concept in Immersion Ultrasonics, Materials Evaluation, May 1968, pp. 83–89.

*Primary Examiner*—Richard C. Queisser
*Assistant Examiner*—John P. Beauchamp
*Attorney, Agent, or Firm*—Karl F. Ross; Herbert Dubno

[57] ABSTRACT

Device for nondestructive ultrasonic testing of cylindrical parts, comprising a basin in which the part to be tested, for example a journal bearing provided with an antifriction alloy is immersed. The basin is mounted on a revolving plate having a gear driven by means of an inclined-tooth pinion. A vertically movable horizontal arm, depending upon diameter of the part to be tested, carries two piezoelectric transducers and an arcograph, the marking of the bonding fault area on the surface of the part to be tested being effected by means of an electric arc produced between one trace element of the arcograph, which receives a voltage signal from the monitor of a fault detector through the control assembly of the arcograph, and the inner surface of the part to be tested. The entire cylindrical surface is explored along a tangent of partially superposed helixes and the pitch of the helix is equal to, or smaller than the diameter of the piezoelectric transducer crystal.

5 Claims, 9 Drawing Figures

DEVICE FOR NONDESTRUCTIVE ULTRASONIC TESTING OF CYLINDRICAL PARTS

FIELD OF THE INVENTION

The present invention refers to a device for ultrasonic nondestructive testing, of the cylindrical parts, for example, of an antifriction alloy for the steel body of a journal bearing.

BACKGROUND OF THE INVENTION

An apparatus is known, for the nondestructive ultrasonic testing of bearing boxes, in which a turn-table is provided with a basin in which the bearing box is immersed.

A number of piezoelectric transducers, which sweep the inner surface of the bearing box during its rotation, are centrally and vertically disposed one under another.

The piezoelectric transducers are connected with a fault detector having a monitor and a recorder. In case a linkage or porosity fault appears at the metal walls of the bearing box, the monitor becomes effected to transmit on electric signal to the recorder, which marks the fault on paper in spot form.

That apparatus has the disadvantage that the bearing boxes to be tested are checked only over an angle of 180° and, in order to locate the fault, one must know the starting point, and then one must transpose the recording onto the actual scale of the bearing box. Furthermore, it does not allow the testing of different types of bearing boxes (regarding their diameters and heights) and poses problems for the very high bearing boxes, requiring a large number of sensors.

Another ultrasonic automatic test apparatus, for tube welds provides a distinct simultaneous recording of the fault on a drum, using a vertical rod provided with a radial arm on which a feeler is mounted, the rod moving in a fixed nut, thus creating a helical control movement at the level of the welded area.

That apparatus has the disadvantage that it requires contacts between the feeler and the fault detector in order to permit the helical movement of the feeler, thereby introducing contact error.

A device is also known for determining ultrasonically faults on long metal bodies, such as welding areas, the part to be tested rotating continuously, step by step, around its own axis, passing through an electrolyte recipient in which the supersonic echo sounder is immersed. Near the supersonic echo sounder there is a fixed electrode, the fault signal received from the ultrasonic apparatus produces an electric field between the electrode and the surface of the part, the fault area being marked by an electroplating on the surface of the part to be tested.

That device has the disadvantage of the long time required by electroplating and by the moving of the welded part to be tested.

SUMMARY OF THE INVENTION

The present invention obviates the above mentioned disadvantages by using a basin in which the part to be tested is immersed. The basin being mounted on a revolving plate having a gear driven by means of an inclined-tooth pinion. The marking is carried out by combining the rotary motion of the part to be tested with the vertically translatory motion of a horizontal arm. The arm is moved by a screw driven by two changeable gears having different numbers of teeth horizontal arm being mounted, as a function of the diameter of the part to be tested. Two piezoelectric transducers are carried by the arm, the marking of the linkage fault area on the surface of the part to be tested being effected by means of an electric arc produced between an element of the arcograph which receives a voltage signal from the monitor of a fault detector through the control assembly of the arcograph. The inner surface of the part to be tested is explored along helixes, the pitch of the helix being equal to, or smaller than the diameter of the piezoelectric transducer crystal.

BRIEF DESCRIPTION OF THE DRAWINGS

FIG. 4b is a section along line A—A of the piezoelectric transducers stand of FIG. 4a.

SPECIFIC DESCRIPTION

Figure 1:
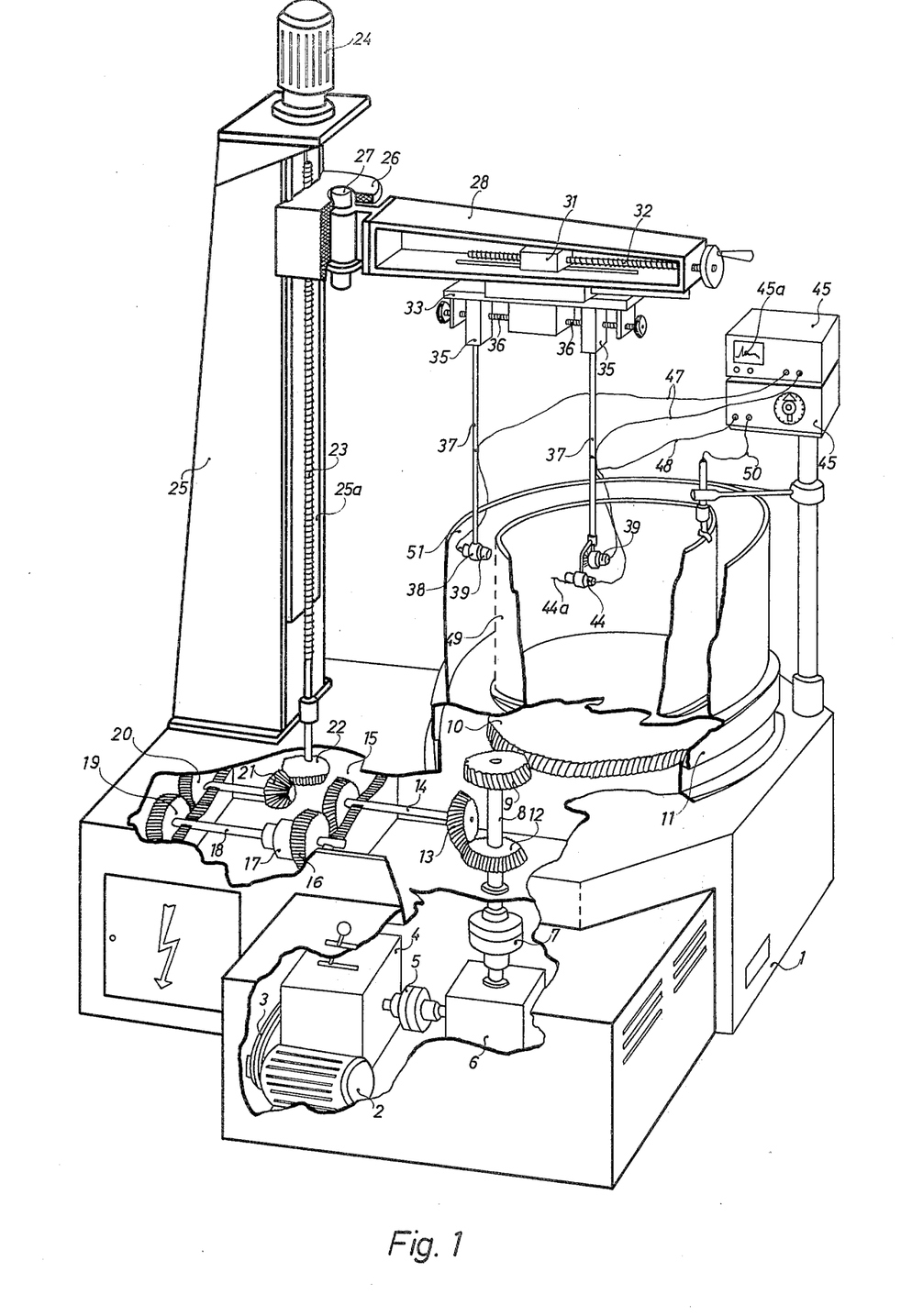
FIG. 1 is an axial perspective view of the device partly broken away.

The device according to the invention comprises a frame carrying an electromotor 2 driving by means of trapezoidal section belts 3 a transmission gearbox 4. The latter drives a worm speed-reduction gear 6 through a flexible coupling 5. The speed reducer 6 drives a vertical shaft 8 through a flexible coupling 7. From the vertical shaft 8, the rotary movement is transmitted to a cylindrical gear train consisting of a pinion 9 and of a gear 10 having inclined toothing. The gear 10 engages a plate 11. There is a bevel pinion 12 on the shaft 8, which intermeshes, with a bevel gear 13 on a shaft 14. The latter carries one of a pair of gears 15, 16 which intermesh the latter gear being free to rotate on its axis.

Through an electromagnetic clutch 17, the rotation of gear 16 is applied to a shaft and then to the change gears 19 and 20, necessary for varying the rate of rotation of the leadscrew and hence the helix pitch.

The movement of the change gear 20 is applied to the bevel pinion 21 and from it, by means of a bevel gear 22 with which it is meshed, to a leadscrew in a vertical plane.

Figure 2:
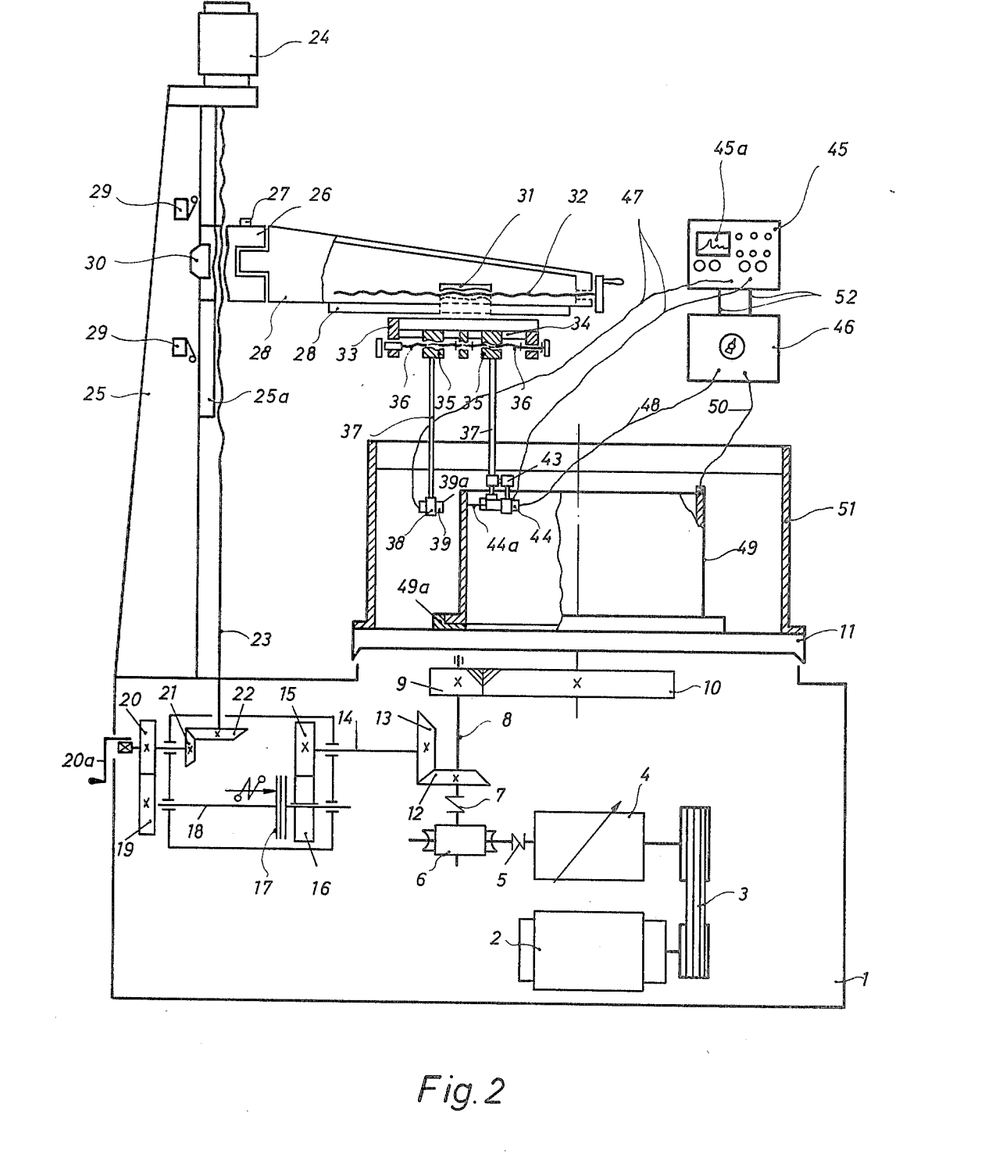
FIG. 2 is a kinematic diagram of the device showing an assembly for recording the fault directly on the surface of the part to be tested.

That movement of the screw 23 can be also effected manually, by means of a crank 20a (FIG. 2).

The leadscrew 23 can be driven by a motor reducer 24 after decoupling of the electromagnetic clutch 17 The motor-reducer is mounted on a vertical column 25 which, in turn, is fastened on the frame 1. The leadscrew motion screw 23 drives a slide 26, gliding on the slide guide 25a of the vertical column 25. There is a horizontal arm 28, a slide track 28a (FIG. 2), mounted on the slide 26 by means of a pivot 27. The horizontal arm 28 can regularly swing horizontally, at certain angles, around the axis of pivot 27. There are also two electric limit stops 29, an upper one and a lower one, mounted on the column 25, and tripped alternately by a cam 30, secured to the slide 26. The electric limit stops 29 define the trip length for the rest slide 26 on the slide track 25a of the column 25.

Figure 3:
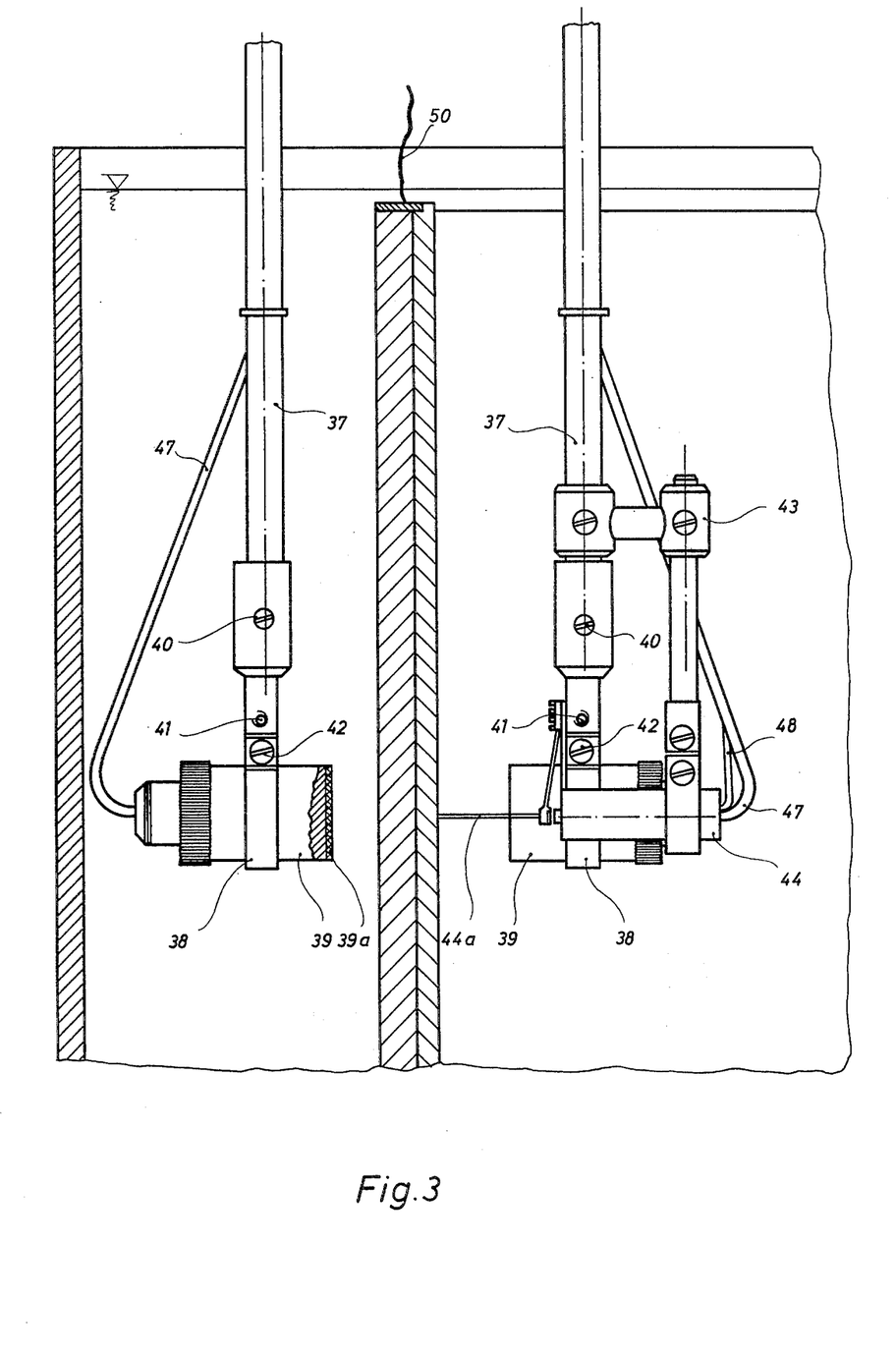
FIG. 3 is a detail view to show the piezoelectric transducers and of the arcograph as to the part to be tested.
Figure 4A:
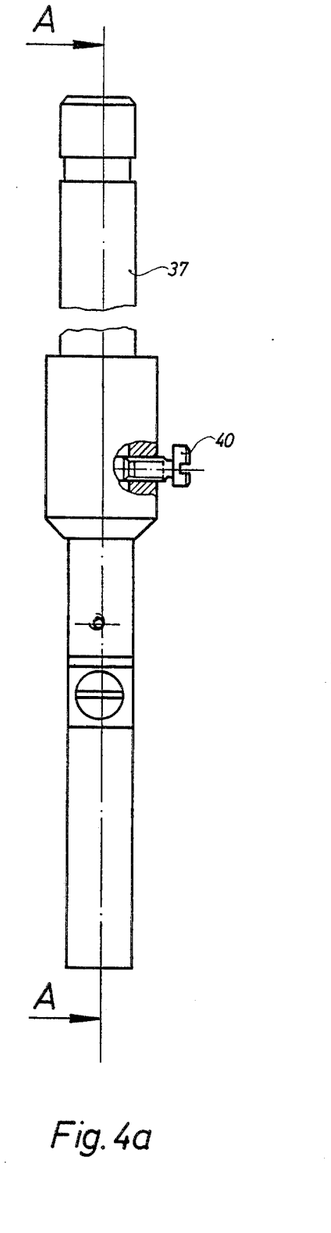
FIG. 4a is an elevational view of the piezoelectric transducer partly broken away.
Figure 4B:
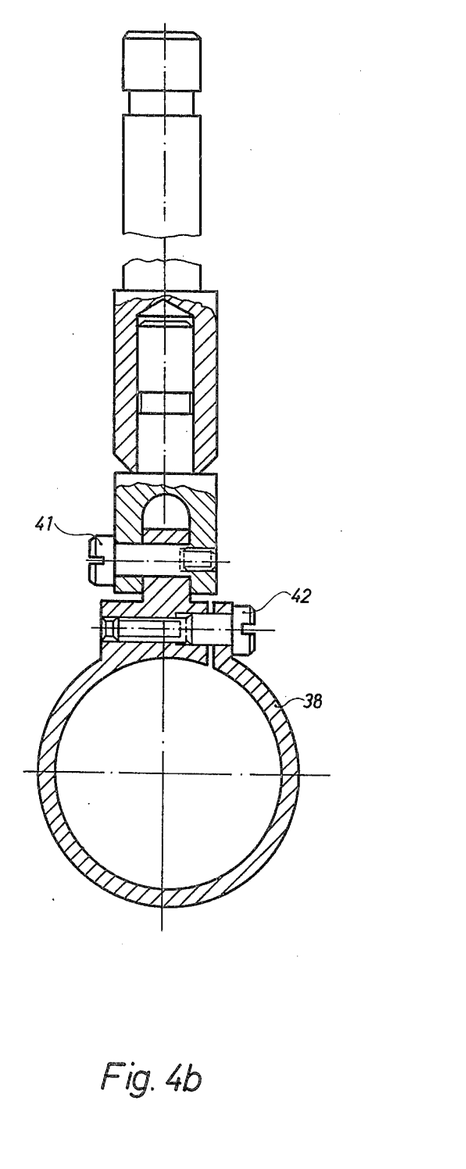

A horizontal slide 31, driven manually by a leadscrew 32, glides on the slide track 28a of the horizontal arm 28. A stand 33, provided with a slide track 34, is fastened on the horizontal slide 31. Two supports 35, independently and manually driven by two screws 36, glide on the slide track 34. There is a rod 37 fixed on each support 35, the lower end of each rod being fixed to a bracket 38. Each bracket carries a piezoelectric transducer 39 (see FIG. 3). Any of the brackets 38 can be individually adjusted, horizontally and vertically, as follows (see FIGS. 3, 4a and 4b):

the screw 40 is loosened to permit the horizontal swivelling of the bracket 38;

the screw 41 loosened to permit the vertical swivelling of the bracket 38.

The piezoelectric transducers 39 are fixed in the brackets 38 by means of screws 42 and sleeves (not represented in the drawing) having their inner diameter equal to the outer diameter of the piezoelectric transducer 39 provided with a piezoelectric crystal 39a.

A bracket 43 is fixed on one of the rods 37 in order to carry an arcograph 44 endowed with a trace element 44a. The bracket 43 has the same adjustement movements as the brackets 38.

Figure 5:
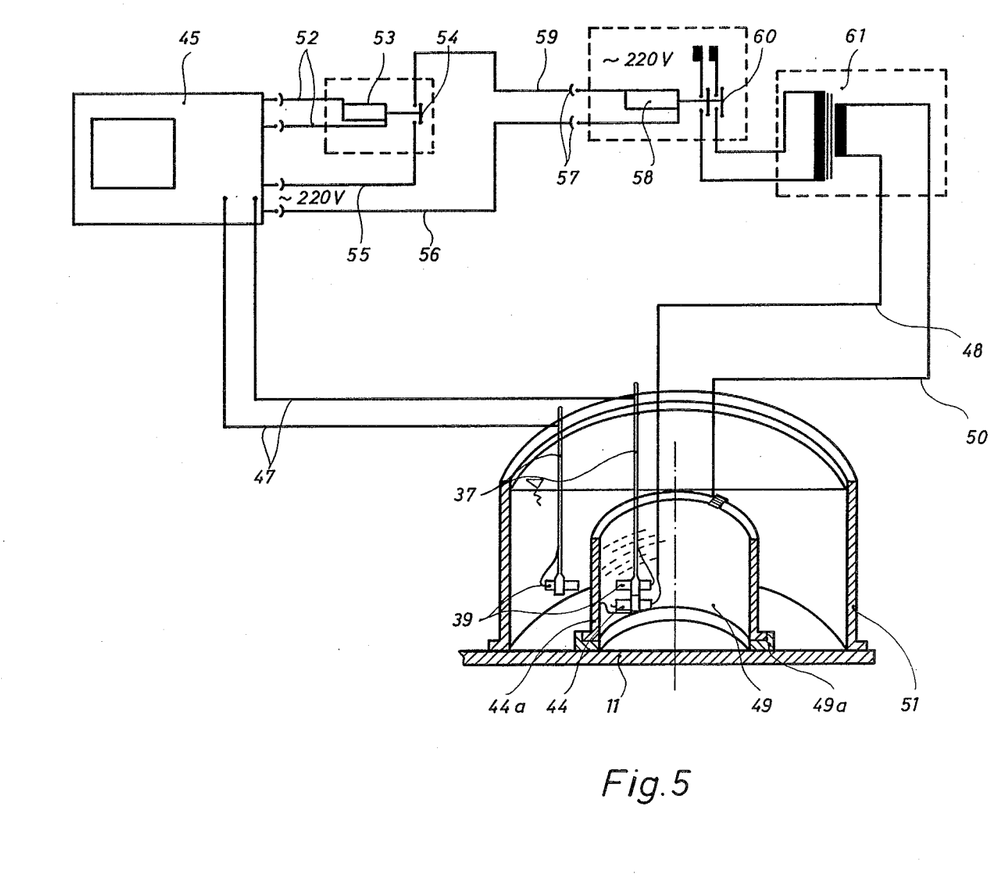
FIG. 5 is a circuit diagram of the control assembly for marking the fault directly on the part to be tested.

The device is provided with an ultrasonic fault detector 45 (see FIGS. 5 and 6) and with a control assembly 46 for the arcograph 44. The connection between the piezoelectric transducers 39 and the ultrasonic fault detector 45 is effected through two cables 47, and connection between the arcograph 44 and its control assembly 46 is effected through a cable 48. The second connection of the control assembly 46 is done with the part to be tested 49 through another cable 50.

The part to be tested 49 is immersed in a basin 51 fixed on the plate 11. The basin 51 has a drain plug (not represented in the drawing). The alignment of the part to be tested 49 on the plate 11 is achieved by means of some channels formed in the plate and of some rings 49a. The control assembly 46 is connected to the ultrasonic fault detector 45 with two cables 52. The cables 52 are connected to a relay 53 provided with contacts (FIG. 5) 54. From the ultrasonic fault detector 45, the cable 55 leads to the contacts 54, and the other cable 56 to the contact 57 belonging to the relay 58. A cable 59 makes the connection between the contacts 54 of the relay 53 and the contacts 57 of the retaining 58. The relay 58 has contacts 60 to which a 220 V voltage is applied. The contracts 60 are connected to the primary of a step-down transformer 61. The cables 48 and 50 connect the secondary of the step-down transformer 61 and the arcograph 44 and the part to be tested 49.

Figure 6:
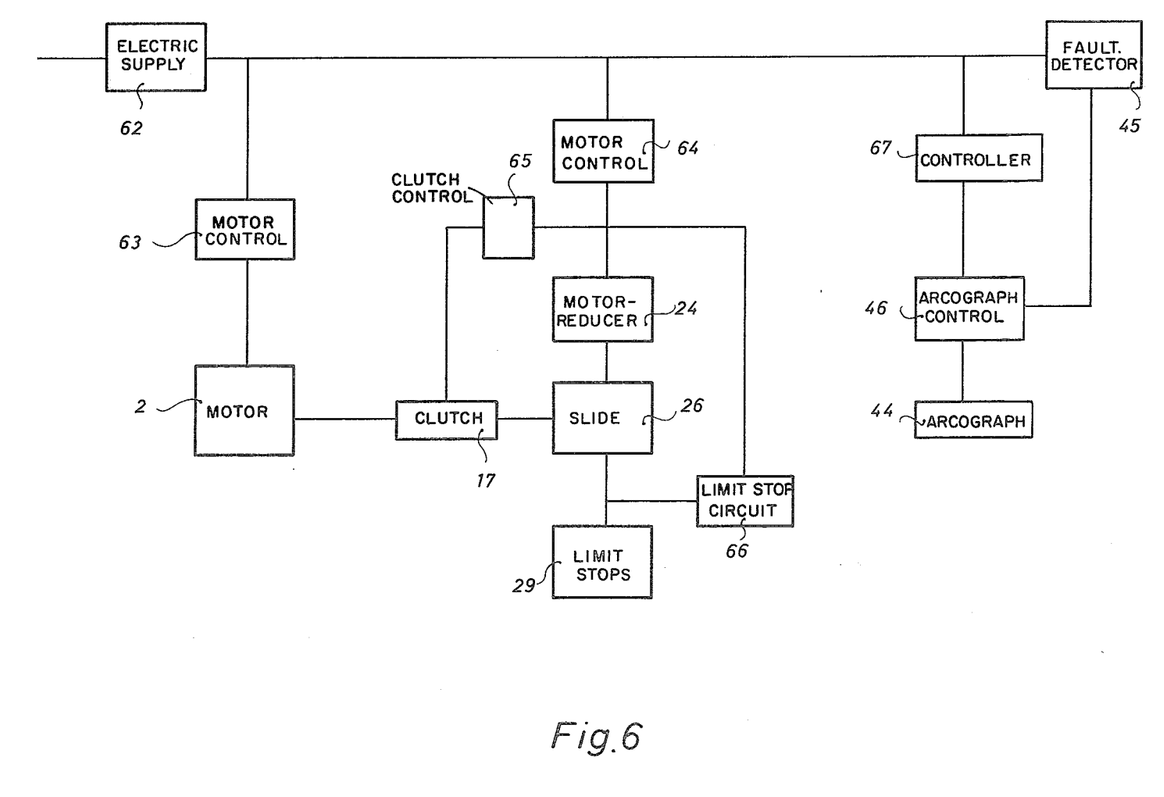
FIG. 6 is a low chart or information diagram for the control equipment in automatic cycle of the device.

The control circuit according to the flow chart represented in FIG. 6 includes:

a circuit 62 for the electric supply of the device, to which a control circuit 63 of the electromotor 2 and also a control circuit 64 of the motor-reducer 24 are connected.

a control circuit 65 of the electromagnetic clutch 17 and a control circuit 66 of the limit stops 29 which determine the length of the path of slide 26. The control circuit 62 is connected to the control assembly 46 of the arcograph 44a and to the ultrasonic fault detector 45 by means of an intermediate control 67.

The device, according to the invention, functions as follows:

One energizes the control circuit 62 of the general of the device, then, the control circuit 63 is activated thus starting the electromotor 2 which, via the transmission gearbox 4, the reduction gear 6, the vertical shaft 8, the pinion 9 and the gear 10, rotates the plate 11 and the basin 51 in which the part to be tested 49 (for example a journal bearing provided with an antifriction alloy layer whose bond to the steel body is to be tested) is immersed.

The device also effects a vertically translatory motion of the arm 28. By means of the pinion 12 and the bevel gear 13, the movement of the vertical shaft 8 is applied to the shaft 14, to the gear 16. The electromagnetic clutch 17, in an "ON" position ordered by the control circuit 65, allows the couples the drive to the leadscrew 23 and to the slide 26, on which the horizontal arm 28 is pivotally mounted, through the shaft 18, the change gears 19 and 20, the bevel pinion 21 and the bevel gear 22.

By combining the horizontal rotary motion of the part to be tested together with the basin 51 and with the plate 11, with the vertically translatory motion of the horizontal arm 28 together with the piezoelectric transducers 39, the entire surface of the part to be tested 49 is scanned on a helical path with a pitch smaller than or equal to the diameter of the piezoelectric crystal 39a of the transducer 39, thus providing partial superposition of the areas tested, in successive rotations, by the transducers.

The path has a constant pitch for the same pair of change gears 19 and 20 independently of the rotative speed of the plate 11 which can be modified as a function of the diameter of the tested part 49 by use of the transmission gearbox 4.

Replacing the pair of change gears 19 and 20 by other pairs of change gears, one can obtain helical paths of different pitches in accordance with the diameters of the piezoelectric crystals 39a of the most desirable transducers 39.

To obtain rapid vertical movement of the horizontal arm 28 after ending the test operation, the motor-reduces 24 is started at its control circuit 64 which, at the same time, decouples the electromagnetic clutch 17 through the control circuit 65.

As it is necessary to limit the trip length of the horizontal arm 28, the device is provided with the aforementioned limit stops 29, fixed upon the vertical column 25, which function as follows.

When the piezoelectric transducers 39 have already traversed the entire height of the part to be tested 49, reaching to its lower end, the cam 30 operates the lower electric limit stop 29, to initiate the operation of the control circuit 66, which acts upon the control circuit 65 of the electromagnetic clutch 17 decoupling declutching it, as well as upon the control circuit 63 of the electromotor 2 turning it off. At the same time the control circuit 64 of the motoreducer 24 starts it. The motor reducer 24 rotates the motion screw 23 to rapidly elevate the horizontal arm 28 until the cam 30 acts upon the upper electric limit stop 29. The upper electric limit stop 29 controls the shut-down of the whole device through its control circuit 66 and the control circuit 64.

The start and the shut-down of the electromotor 2 and of the horizontal arm 28 can be also done manually, by acting upon the control circuits 63 and 64.

The vertical displacement of the horizontal arm 28 can be done also manually with the electromagnetic clutch 17 in its "OFF" position. The positioning of the piezoelectric transducers 39, nearer to or further from the center of the plate 11, depends on the diameters of the parts to be tested. This operation is done manually by means of the leadscrew 32 which moves the horizontal slide 31 on the slide track 28a of the horizontal arm 28.

The distance adjustment of the piezoelectric transducers 39 as to the walls of the part to be tested 49 is done independently for each transducer by manually operating the screws 36. Those screws move the supports 35 together with the piezoelectric transducers 39 on the slide track 34 of the stand 33 bringing them nearer or moving them away in order to get the most favorable working distances. The adjustments are effected only once for the entire set of parts to be tested of the same dimensions.

A journal bearing can be tested as to the quality of bonding to the steel body of an antifriction alloy layer. The basin 51 is filled with water up to a predetermined level. A standard part, whose bonding of the antifriction alloy layer to the steel body is known, is sunk and laligned inside the basin 51. The positions and the distances of the piezoelectric transducers 39 and of the arcograph 44 as to the surface of the standard part are adjusted and at the same time, adjustments are done for the ultrasonic fault detector 45 so that to obtain a maximum transmission pulse on the screen 45a of the fault detector.

The standard part is taken out and the bearing to be tested is immersed and aligned after previously removing a part of the antifriction alloy in order to eliminate the casting irregularities. The electric connection between the part to be tested and the control assembly 46 of the arcograph 44 is realized by means of the cable 50.

As the bonding of the antifriction alloy stratus to the steel body cannot be the same everywhere, the transmission pulse on the screen 45a of the fault detector will have a varying value, its maximum value coresponding to the best linkage.

Assuming an accepted degree of bonding, the monitor of the fault detector is adjusted for that value. All the transmission pulses indicating a degree of bonding less than accepted one will be signaled out by the monitor of the fault detector. All the preliminary operations being finished, the device is started.

The piezoelectric transducers 39 scan the surface of the part to be tested 49 on the helical trajectories mentioned.

When, over a certain area, the degree of bonding of the antifriction alloy layer to the steel body is to the accepted one the transmission pulse on the screen 45a of the fault detector 45 will fall below the accepted value thus making the monitor signal it out.

Thus the contact 54 is closed, energizing the contactor 58 which closes the contacts 60 and applies electric current to the primary of the transformer 61. Within the secondary a voltage is obtained which is applied to the arcograph 44 and to the bearing to be tested 49 through the cables 48 and 50. Thus the bearing closes the coil circuit of the arcograph 44 and the trace element 44a will oscillate between the surface of the part and the coil core, shutting and opening the arcograph circuit thus generating an electric arc between the trace element 44a of the arcograph 44 and the surface of the bearing to be tested 49. That electric arc produces visible traces on the surface of the bearing in the area having a degree of bonding less than the accepted one (see FIG. 7a and FIG. 7b).

Crossing a fault area, the arcograph 44 will trace a line having the length of the fault in that area of the tested bearing. One obtains in this way a number of parallel lines, of different lengths, whose envelope curve determines the shape and the size of the fault as can be seen in FIG. 7a.

Figure 7A:
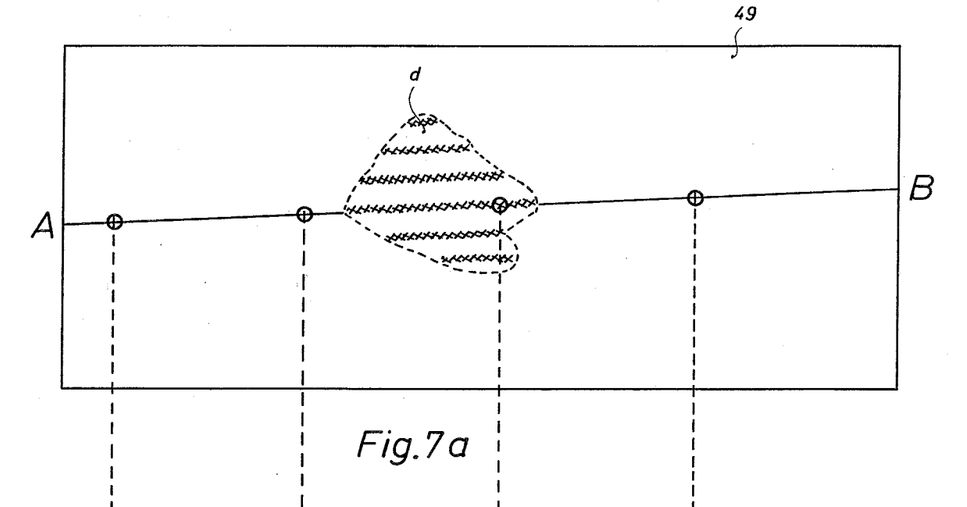
FIG. 7a is a developed surface of a cylindrical part, with the marking of the fault area.

According to FIG. 7a, there are four points having different linkage degrees represented on a measurement trajectory A-B.

Figure 7B:
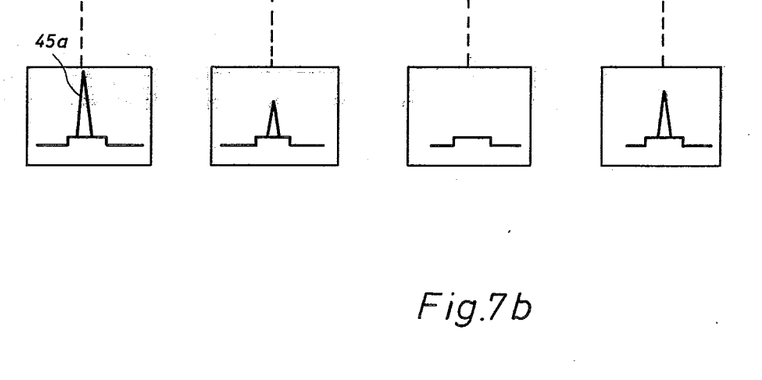
FIG. 7b is a diagram of the transmission pulses obtained on the fault detector screen at different places along a journal bearing, where in which the degree of bonding of the antifriction alloy to the steel body varies from a maximum to a minimum.

FIG. 7b represents the transmission pulses coresponding to those four points. After exploring the entire surface of the bearing 49, the cam 30 acts upon the lower electric limit stop 29 decoupling the control circuit 63 of the electromotor 2 and the control circuit 67 of the arcograph 44. At the same time the motorreducer 24 is started by means of its control circuit 64, elevating the horizontal arm 28 up to its upper position, thus making the upper electric limit stop 29 stop the whole system.

The bearing 49 is taken out of the device when the control operation is finished.

We claim:

1. A device for the nondestructive testing with ultrasonics of cylindrical parts, comprising:
    a turntable provided with a basin adapted to receive a cylindrical part to be tested and provided with a gear;
    a pinion meshing with said gear;
    drive means for rotating said pinion;
    a vertically disposed leadscrew;
    a pair of change gears operatively connecting said leadscrew with said drive means;
    a horizontal arm vertically displaced by said leadscrew and overhanging said part;
    a pair of piezoelectric transducers carried by said arm for scanning said part;
    an arcograph carried by said arm and having a trace element energizable to mark a fault directly on the part scanned by said transducers; and
    a fault detector connected to said piezoelectric transducers and operatively connected to said arcograph for energizing said trace element upon detection of a fault by said transducers, said transducers sweeping along the surfaces of said part a generally helical path of a pitch determined by the relative rates of rotation of said turntable and said leadscrew.

2. The device defined in claim 1 wherein the pitch of the helical path is at most equal to the diameter of one of said piezoelectric transducers.

3. The device defined in claim 1 wherein said change gears are replaceable with gears of different numbers of teeth to maintain the pitch of the helical path at most equal to the diameter of one of said transducers for cylindrical parts to be scanned of different diameters.

4. The apparatus defined in claim 1, further comprising a support carrying said drive means, said gears, said turntable and said leadscrew, said support having a post extending along said leadscrew and provided with a vertical track, said arm being provided with a slide guided along said track and driven by said leadscrew, said arm being formed with a horizontal track, each of said piezoelectric transducers being mounted on a respective arm dependent from said horizontal track and formed with respective slides guided thereon, manual adjusting means for positioning the slides of said rods along said horizontal track, said leadscrew being provided with further drive means for rapidly displacing said horizontal arm in a direction opposite the direction of displacement thereof by said change gears.

5. The device defined in claim 4, further comprising an electromagnetic clutch for decoupling said leadscrew from the first-mentioned drive means during operation of the leadscrew by said second drive means.

* * * * *